(12) United States Patent
Niskanen et al.

(10) Patent No.: US 8,664,001 B2
(45) Date of Patent: Mar. 4, 2014

(54) IMMUNOCHEMICAL FILTER DEVICE AND METHODS FOR USE THEREOF

(75) Inventors: Aimo Niskanen, Espoo (FI); Mika Saramaki, Karkkila (FI)

(73) Assignee: Ani Biotech Oy, Helsinki (FI)

( * ) Notice: Subject to any disclaimer, the term of this patent is extended or adjusted under 35 U.S.C. 154(b) by 600 days.

(21) Appl. No.: 10/954,627

(22) Filed: Sep. 29, 2004

(65) Prior Publication Data

US 2005/0277203 A1 Dec. 15, 2005

(30) Foreign Application Priority Data

Jun. 15, 2004 (FI) .................................... 20040825

(51) Int. Cl.
*G01N 1/18* (2006.01)

(52) U.S. Cl.
USPC ........... 436/177; 436/174; 436/178; 436/518; 436/535; 435/7.1; 435/283.1; 435/287.1; 435/288.1; 422/50; 422/400; 422/411; 422/407; 422/420

(58) Field of Classification Search
USPC ........ 435/4–7.1, 7.93–7.95, 67, 287.1, 287.2, 435/287.7–287.9; 422/55, 56, 58, 59–61, 422/70; 436/8, 18, 164, 165, 169, 170, 501, 436/514, 578; 220/259, 375, 367.1
See application file for complete search history.

(56) References Cited

U.S. PATENT DOCUMENTS

| | | | |
|---|---|---|---|
| 3,990,852 A | 11/1976 | Piazzi et al. | |
| 4,562,147 A | 12/1985 | Joo | |
| 4,598,051 A * | 7/1986 | Papahadjopoulos et al. | 435/7.25 |
| 4,757,002 A | 7/1988 | Joo | |
| 4,960,691 A * | 10/1990 | Gordon et al. | 435/6 |
| 5,078,968 A * | 1/1992 | Nason | 422/58 |
| 5,124,041 A * | 6/1992 | Sheer et al. | 210/641 |
| 5,420,016 A * | 5/1995 | Boguslaski et al. | 435/12 |
| 5,624,554 A * | 4/1997 | Faulkner et al. | 210/232 |
| 5,736,188 A * | 4/1998 | Alcock et al. | 427/2.11 |
| 5,849,065 A * | 12/1998 | Wojke | 96/211 |
| 5,849,505 A * | 12/1998 | Guirguis | 435/7.2 |
| 5,877,028 A * | 3/1999 | Chandler et al. | 436/514 |
| 6,145,688 A * | 11/2000 | Smith | 220/259.3 |
| 6,162,398 A | 12/2000 | Shuter | |
| 6,375,028 B1 | 4/2002 | Smith | |
| 6,524,530 B1 * | 2/2003 | Igarashi et al. | 422/411 |
| 6,632,681 B1 * | 10/2003 | Chu | 436/178 |
| 6,649,418 B1 | 11/2003 | Geisberg | |
| 6,737,277 B1 | 5/2004 | Kang et al. | |
| 6,869,405 B2 * | 3/2005 | Marsden | 600/573 |

(Continued)

FOREIGN PATENT DOCUMENTS

| | | |
|---|---|---|
| EP | 0392377 | 10/1990 |
| EP | 0 250 137 | 8/1992 |

(Continued)

*Primary Examiner* — Melanie Y Brown
(74) *Attorney, Agent, or Firm* — DLA Piper LLP (US)

(57) ABSTRACT

An immunochemical filter device which has filter material attached to a support member (such as a cap) which is, in turn, attachable to a sample collection vessel. The filter material includes a labeled binding reagent that is released from the filter material into solution by migration of a liquid sample solution through the filter material. The mixture of the sample solution and the labeled specific binding reagent is transferred to an analyzer device for performance of a method for determining the presence or absence of an analyte in a sample solution.

5 Claims, 3 Drawing Sheets

(56) References Cited

U.S. PATENT DOCUMENTS

| | | | |
|---|---|---|---|
| 7,378,054 B2* | 5/2008 | Karmali | 422/410 |
| 7,497,997 B2* | 3/2009 | Glezer et al. | 422/504 |
| 8,133,454 B2* | 3/2012 | Tajima | 422/501 |
| 2002/0042145 A1* | 4/2002 | Forsberg | 436/165 |
| 2002/0173047 A1* | 11/2002 | Hudak et al. | 436/178 |
| 2003/0049857 A1* | 3/2003 | Chan | 436/170 |
| 2003/0064423 A1* | 4/2003 | Gordon et al. | 435/7.92 |
| 2004/0002063 A1* | 1/2004 | Chan et al. | 435/5 |
| 2004/0013575 A1* | 1/2004 | Stevens et al. | 422/102 |

FOREIGN PATENT DOCUMENTS

| | | |
|---|---|---|
| EP | 0 291 194 | 2/1994 |
| EP | 0 284 232 | 10/2002 |
| WO | WO 86/03839 | 7/1986 |
| WO | WO 03/098215 | 11/2003 |

\* cited by examiner

IMMUNOCHEMICAL FILTER DEVICE AND METHODS FOR USE THEREOF

CROSS-REFERENCE TO RELATED PATENT APPLICATIONS

This application claims the benefit of the priority of Finnish Patent Application No. FI 20040825 filed on Jun. 15, 2004.

FIELD OF THE INVENTION

The present invention relates to an immunochemical filter device, comprising a filter material attached to a support member, wherein the filter material comprises a labeled binding reagent.

BACKGROUND OF THE INVENTION

Methods and devices based on immunodiffusion are known from for example U.S. Pat. No. 4,757,002, U.S. Pat. No. 3,990,852 and U.S. Pat. No. 4,562,147. Immunochromatographic methods based on lateral flow are known from EP 0 291 194, EP 0 284 232, EP 0 250 137, and WO 86/03839. A diagnostic device comprising a post-filter unit is known from U.S. application 2003/0049857.

U.S. Pat. No. 4,562,147 provides a radial immunodiffusion enzyme assay method for testing of pseudorabies antibodies in swine and other animals. Agar test plates are provided including an underlying adherent coating of solubilized non-infectious swine pseudorabies antigen. The result of the test is obtained from the diameters of the resulting colored zones which correlate with the titers obtained by the official virus neutralization test.

EP 0 291 194 relates to assays involving specific binding, especially immunoassays and devices therefore. The analytical test device comprises a hollow casing, containing a dry porous carrier, which communicates indirectly with the exterior of the casing via a bibulous sample receiving member. The carrier contains in a first zone a labeled specific binding reagent and in a second zone spatially distinct from the first zone an unlabelled specific binding reagent for the same analyte. When the test is performed the sample solution is contacted with the test device directly which increases the risk of overflow to the second zone.

EP 0 284 232 provides a solid phase assay for determining the presence or absence of analyte in a liquid sample. A test strip of the invention has a tracer movably supported on a first portion and a binder immobilized on a second portion. A disadvantage of this method is that the sample solution is contacted with the test during the performance of the test, which increases the risk of overflow to the second portion.

EP 0 250 137 describes an immunoassay using colloidal gold for detecting a ligand in a sample, where a membrane strip is contacted with a sample and simultaneously or successively with a liquid reagent containing a ligand binding partner or ligand labeled with colloidal gold. A disadvantage of this method is that an additional liquid reagent containing the labeled ligand is needed.

WO 86/03839 illustrates a solid phase diffusion assay where the sample is first mixed with a labeled binding substance and then applied to a region of a support with immobilized adsorbent molecules and allowed to diffuse therein. The diffusion pattern is visualized and measured.

US 2003/0049857 relates to a diagnostic device comprising a test unit and a post-filter unit. The post-filter unit comprises a label zone containing a dried indicator reagent. The indicator reagent is drawn trough the post filter unit with a separate buffer and the sample is added directly to the test unit comprising the reaction zone. This however makes the test awkward to use.

It is evident from the description of the background art that a multitude of different test kits are available. A wide variety of test kits are available commercially and many of them are intended for home use. In spite of their convenient formats, there are many risks for errors if they are used in an erroneous manner. This risk is imminent when the test device is used for sampling, which may be both impractical and inconvenient. Especially, when the test device is used as a sampling device or for collecting the sample there is a risk that the sensitive reagents and the structure of the analytical device is destroyed or disturbed. Further solid samples or liquid samples which need to be diluted require an additional step.

The present invention provides an improved detection system for immunochemical tests involving a filter device which enables a liquid sample with or without dilution or a diluted solid sample to be filtered through the device and the sample solution together with the labeled specific binding reagent to be transferred and mobilized from the filter material in a controlled manner. Due to the two-part system the analyzer device is not in direct contact with the liquid sample solution, thereby minimizing the possibilities that the reagents in and the structure of the analyzer device are destroyed or disturbed by the sampling procedure. The device of the present invention is especially advantageous for tests where the sample need to be diluted.

It should be noted that all documents cited in this text ("herein cited documents") as well as each document or reference cited in each of the herein-cited documents, and all manufacturer's literature, specifications, instructions, product data sheets, material data sheets, and the like, as to the products mentioned in this text, are hereby expressly incorporated herein by reference.

SUMMARY OF THE INVENTION

The present invention provides an immunochemical filter device for performing an immunoassay comprising a filter material attached to a support member. The filter material comprises a labeled binding reagent which is released from the filter material by migration of a liquid sample solution therethrough. The support member is preferably a cap-like member that attaches in a liquid tight manner to a sample collection device, such as a tube. The labeled binding reagent/liquid sample solution is expressed from the cap (e.g., through an aperture, diffusible membrane or valve therein) for application to an analytical device (e.g., an immunochromatographic test strip having a binding reagent disposed thereon).

In a preferred embodiment of the present invention the filter device is part of a cap which is liquid tightly attachable to a vessel. The liquid sample solution from the vessel mixed with the labeled binding reagent (preferably a reagent specific for analyte) released by contact with the sample from the filter material are transferred from the filter device to an analyzer device. Suitable analyzer devices include test strips used in lateral flow testing from which the positive or negative results are directly readable. The result can be read directly visually (by naked eye) or by appropriate equipment capable of recording the results. The sample solution may contain the sample as such or diluted with a buffer solution or extraction buffer.

An immunochemical process of the present invention for determining the presence or absence of an analyte in a sample solution is also provided. The process comprises the steps of adding a liquid sample to a vessel, attaching a filter device comprising a filter material attached to a support member liquid tightly to the vessel wherein the filter material comprises a labeled binding reagent, causing the sample to migrate through the filter material, contacting the mixture of the sample and the labeled binding reagent with an analyzer device and reading the result by detecting the presence or absence of said analyte in the analyzer device.

The present invention further relates to a kit for determining the presence or absence of an analyte in a sample. The kit comprises the test device of the invention and a vessel (e.g., a sample collection vessel) whereto the filter device is liquid tightly attachable. The filter device comprises a filter material attached to a support member (e.g., a cap) wherein said filter material comprises a labeled specific binding reagent. Further an analyzer device comprising a porous carrier wherein said porous carrier lacks a labeled specific binding reagent may be part of the kit.

DETAILED DESCRIPTION OF THE PREFERRED EMBODIMENTS

The present invention relates to an immunochemical filter device for performing an immunoassay wherein the filter device comprises a filter material attached to a support member. The filter material comprises a labeled binding reagent, preferably one specific for analyte. The labeled specific binding reagent is released from the filter material by migration of a liquid sample solution through the filter material.

In a preferred embodiment the support member is a cap of a vessel, for example a sample collection tube, and said cap is liquid tightly attachable to the tube. Said cap preferably includes an aperture, diffusible membrane or valve through which liquid sample solution, after contact with labeled binding reagent, may be caused to flow from the filter device.

The invention further provides a detection system comprising an immunochemical filter device and an analyzer device, where the mixture of sample solution and labeled specific binding reagent or the reaction product (complex) formed thereof are added to the porous carrier of the analyzer device comprising a specific binding reagent optionally immobilized on the porous carrier. Normally the liquid expressed from the filter device through the aperture in the cap moves throughout the porous carrier of the analyzer device by diffusion and/or capillary action.

The present invention also relates to a kit for determining the presence or absence of an analyte in a sample, comprising a filter device comprising a filter material attached to a support member and a sample collection vessel whereto the filter device is liquid tightly attachable. The filter material comprises a labeled binding reagent, preferably one specific for analyte.

Figure 1:
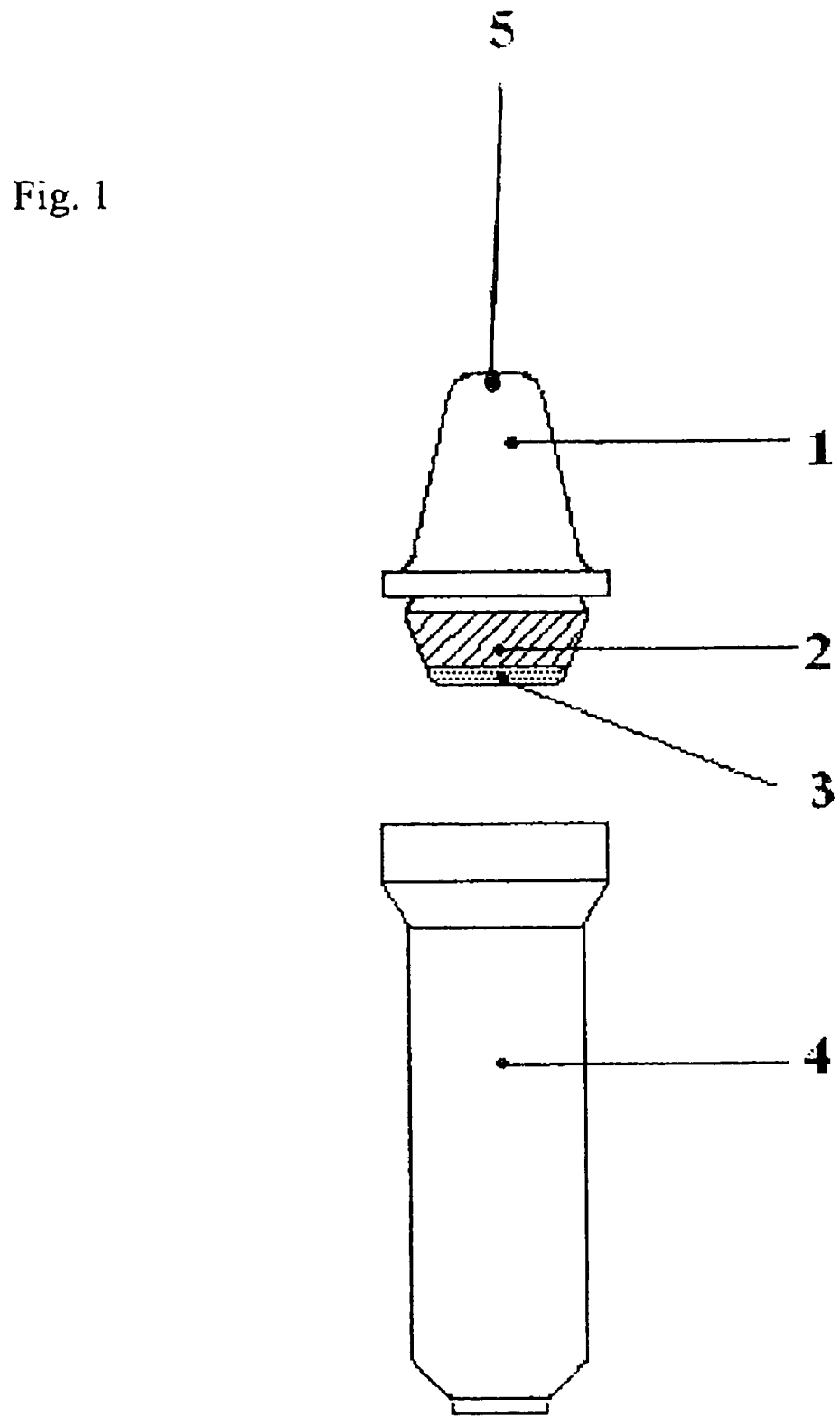
FIG. 1 is a side view of a filter device and a vessel in accordance with the invention.

Turning to FIG. 1, a filter device and a vessel in accordance with the invention are shown. A filter material 2 comprising a labeled specific binding reagent 3 in one end is attached to a transparent cap 1, in which an aperture 5 is disposed. The filter device is attachable at an end opposing aperture 5 to a sample collection vessel 4.

Figure 2:
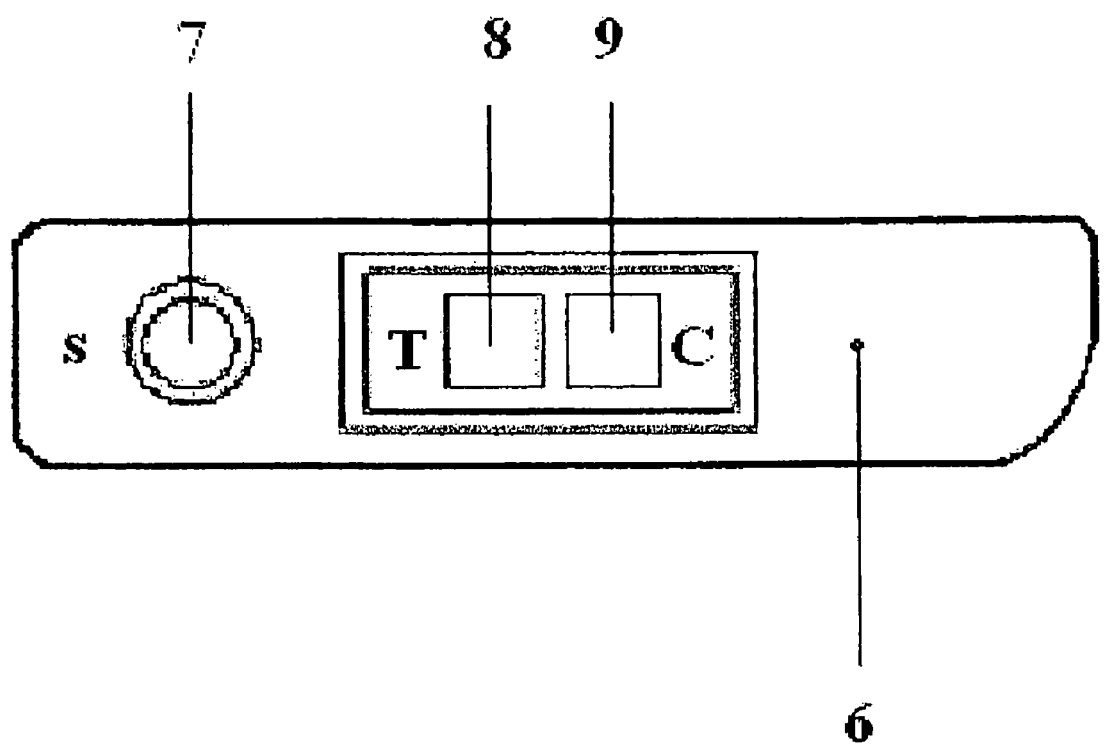
FIG. 2 is a view seen from above of an analyzer device.

FIG. 2 shows a view seen from above of an analyzer device. A casing 6 comprises a sample well 7 where the mixture of sample solution and conjugate solution is transferred. The detection zone of the porous carrier is placed in the test window 8 and in case of a positive result a visible reaction can be seen there. The control zone of the porous carrier is placed in the control window 9 where a visible reaction should be seen whenever the test is performed.

Figure 3:
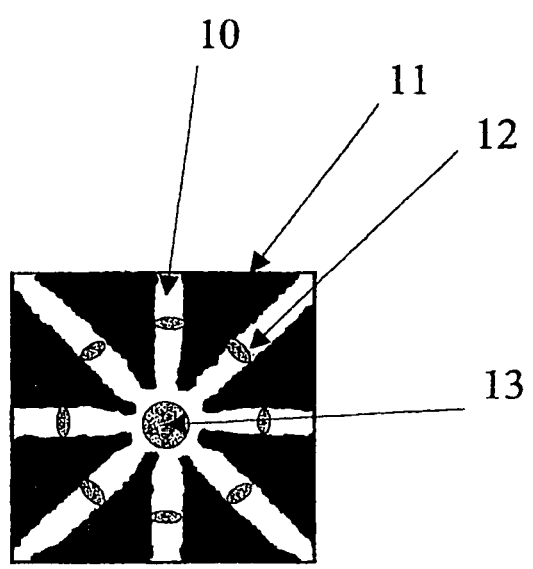
FIG. 3 is a view seen from above of another embodiment of the analyzer device.

FIG. 3 is a view seen from above of another embodiment of the analyzer device. Eight channels 10 are made by laser-etching a figure on a porous carrier such as nitrocellulose film. Treated areas 11 where markings concerning the tests and the manufacturer may be added during the laser treatment separate the channels. Each channel 10 comprises a specific binder in a detection zone or dot 12. Also a place 13 (sample receiver) where the mixture of sample solution and conjugate solution should be transferred is shown.

The immunochemical filter device enables a controlled mobilization and mixing of the labeled specific binding reagent with a potential analyte of the sample solution in the analyzer device comprising a porous carrier. In other words the labeled specific binding reagent is mobilized in a controlled manner when transferred to the analyzer device comprising a porous carrier. Thereby a more sensitive method for detecting different analytes in samples is provided. Furthermore, since the filter device also filters the sample, a sensitive and hygienic test is provided. Solid particles of a faeces sample or another solid sample will not penetrate or permeate the filter and will thus not block the pores of the analyzer device. If a vessel is used, the solid particles stay in the vessel thus providing a hygienic test.

The analytes to be detected can be disease specific antibodies including IgG, IgM and IgA, antibodies against *Helicobacter pylori*, antigens such as Myoglobin and Troponin, Toxoplasma, *Chlamydia trachomatis* and pneumonia, *Bordetella pertussis, Mycoplasma pneumoniae*, Hepatitis A, B, C, HIV1,2, respiratory disorders or etc., autoantibodies against human proteins, viruses from faeces including Rota, Adeno, Parvo, Astro or Distemper, antigens excreted to the urine including Luteinizing hormone (LH), Follicle stimulating hormone (FSH) and human chorionic gonadotropin (hCG) or to faeces including *H. pylori*, samples taken with a swab such as Group A Streptococci, Chlamydia antigen tests, Candida, Trichomonas or other antigens of or antibodies against bacteria, virus, fungi and parasites or components and products thereof.

The device and method of the invention may be used for a multitude of different tests including pregnancy, menopause, fertility, C-reactive protein (CRP), Thyroid stimulating hormone, toxoplasmosis, cancer antigen, respiratory disorder, bacteria, viruses, venereal diseases, celiac disease, allergy, myocardial infarct and drug tests, etc.

In preferred embodiments of the invention the kit may further comprise a buffer solution wherein said buffer solution is added to the vessel in order to make the test kit ready to use or an analyzer device comprising a porous carrier wherein said porous carrier lacks a labeled specific binding reagent. Further positive or negative controls, a sampling device, for example a capillary, pipette or swab may be included. In order to provide everything needed to perform a certain test also lancets, alcohol pads and plasters may be included in the kit.

The sample can be urine, faeces, blood, serum, plasma, saliva, mucus, excretion from eyes or the sample solution may be a mixture of a sample and a buffer solution.

The present invention is advantageous for tests where the sample have to be diluted in order to perform a test. This does not require an additional step when the present invention is used since the sample may be added to a vessel already containing a suitable buffer solution. Further the sample is easy and hygienic to handle and the risk of contamination is decreased. Solid samples for example faeces are one example of samples which need to be diluted. Furthermore for example many whole blood samples such as finger tip samples (10 µl) usually have to be diluted 1/50 to 1/200 in order to be able to perform certain tests. This applies for instance to CRP-tests where the sample has to be diluted with a buffer solution in order to obtain a suitable sample solution.

The buffer of the buffer solution is chosen from buffers known in the art and depends on the detected analyte. The pH is usually between 7 and 8.5 and the capacity of the buffer is sufficient to maintain the pH. The buffer solution may further comprise additives in order to stabilize or increase or decrease other features of the buffer solution. The buffer solution may be added to the vessel of the kit beforehand and can thus be included in a kit of the present invention.

The filter device of the present invention is especially advantageous for determining for example *Helicobacter pylori*. The filter device is a filter tip comprising an antibody against *H. pylori* or an *H. pylori* antigen dried as a part of a conjugate solution on the filter material. If *H. pylori* antibodies are detected from whole blood or serum samples an *H. pylori* antigen is used and if the sample is faeces an antibody against *H. pylori* is added to the filter tip.

Another advantageous use of the test device of the present invention is for determining celiac disease wherein the filter device in the form of a filter tip comprises a tissue protein or anti human IgA specific antibody against transglutaminase.

The filter device is dried to a moisture content of 8% or less and packed hermetically separately or in combination with said analyzer device.

Constructing the Filter Device

The construction of the filter device comprises the steps of: treating a filter material attached to a support member with a conjugate solution comprising a labeled specific binding reagent and optionally additives, and further drying, and packing the device. The support member is provided with an aperture, diffusible membrane and/or valve (preferably one openable on application of gentle pressure; i.e., on pressure of the cap against the sample well of an analytical immunochemical device).

Different filter materials known in the art are possible to use. Preferably a hydrophilic permeable material such as polyethylene, polyester, glass fiber and mixes thereof is selected. The particle retention of the filter material is preferably 1 to 25 micrometers, more preferably 10 to 20 micrometers.

Adding the Specific Labeled Reagent

The filter material of the filter device is impregnated with a conjugate solution comprising a specific labeled reagent. The whole material may be impregnated but preferably the conjugate solution is added in the middle of one side of the filter material and impregnated as a thin layer on top of the filter material. The preferred amount of conjugate solution is 1 to 100 µl, preferably 10 to 40 µl. If the filter device comprises a filter tip or cap which is liquid tightly attachable to the vessel, the conjugate solution is dispensed at that end which is put inside the vessel.

The labeled specific binding reagent is obtained by coating the label particles with specific binding reagent(s) using methods well known in the art. The specific reagents of the filter device and the analyzer device include antibodies, antibody fragments, recombinant antibodies, recombinant antibody fragments, antigens, lectins, receptors and/or ligands. The label applicable in the filter device includes colored latex, gold, metal, dye, fluorogenic substances, superpara-magnetic particles coated with the specific binders. Chromogenic substances, particularly fluorochromogens and enzymatic labels may be used as markers as well. It is possible to use a combination of several different labeled specific binding reagents if the sample is detected for more than one analyte and the same specific binding reagent cannot be used for all.

The labeled specific binding reagent may be added to the filter material as such or as a conjugate solution further comprising additives for example natural or synthetic polymers such as albumin (BSA, Bovine serum albumin) and casein or PEG (polyethylene glycol), PVA (polyvinyl alcohol) and PVP (polyvinyl pyrrolidone), nonionic detergents such as TWEEN 20, HEXA (hexane sulphonic acid), TRITON-X-100, SDS and BRIJ and preservation agents such as sugar, for example glucose, sucrose and trehalose or derivatives thereof. Additives are added as stabilizers in order to increase stability, in order to improve the release of labeled specific binding reagent and as blocking agents in order to make the reactive sites of the filter material inert when the test is performed and the conjugate solution is activated by a sample solution. The conjugate solution may be applied by hand with a pipette or with an automated dispenser.

Drying and Packing the Device

The filter device is dried in a dry room, with a relative humidity less than 20% and further in a dry room with a relative humidity less than 8%. The filter device is then packed hermetically separately or in combination with an analyzer device, for example in a hermetic pouch.

Preparing the Analyzer Device

The mixture of a sample solution and a labeled specific binding reagent may be transferred to an analyzer device, which is the result recording detecting device of the detection system. The analyzer device may be prepared by immobilizing one or more specific binding reagents and optionally also control reagents directly or indirectly to a porous carrier of the device. The porous carrier is thereafter blocked. The blocking solution, a mixture comprising natural or synthetic polymers such as albumin (BSA, Bovine serum albumin) and casein or PEG (polyethylene glycol), PVA (polyvinyl alcohol) and PVP (polyvinyl pyrrolidone), nonionic detergents such as TWEEN 20, HEXA (hexane sulphonic acid), TRITON-X-100, SDS and BRIJ and preservation agents such as sugar, for example glucose, sucrose and trehalose or derivatives thereof, is prepared in order to make the reactive sites of the porous carrier inert.

The porous carrier of the analyzer device is preferably selected from a group of materials consisting of nitrocellulose, paper, glass fiber, nylon, polyester, polysulphonate or cellulose and derivatives thereof and the porous carrier can optionally be placed on a backing and/or in a casing. The analyzer device of the present invention differs from the conventional prior art devices in that it lacks the mobilizable labeled specific binding reagent.

It is obvious for one skilled in the art that the filter device can be used in connection with a analyzer device where the porous carrier comprises one porous passage, which may be penetrated by a sample solution, containing detection zone(s) but also with an analyzer device where the porous carrier comprises two or more channels optionally made by a suitable method comprising at least one specific binding reagent per channel, immobilized as a dot or zone. A multiple channel device can be prepared by treating a porous material with a suitable method in order to get different channels for tests of different analytes (or controls). Thus several analytes can be detected from the same sample by one single test. Furthermore several detection zones per channel may be added in order to perform a semi-quantitative test. The analyzer device may further comprise for example a sample pad comprising polyester or glass fiber.

Different types of analyzer devices are described in background art. Devices with multiple channels enable testing of several analytes simultaneously. Markers specific for different analytes can be grouped together to form different products. The multiple channel device comprises a porous carrier processed by a water-repellency treatment or by laser in order to cause a network of channels where the tested sample can migrate. Different specific binding reagents may be bound in each channel. Multiple channel analyzer devices have been described for example in PCT/FI2004/000179.

In another preferred embodiment of the invention a multiple channel analyzer device is used in order to detect for several analytes from the same sample at the same time. Every channel of such device can thereto have several detection zones and/or control zones.

The embodiments described in the Figures and the Examples are only to be seen as examples of embodiments which are within the scope of the invention. They should not be considered to limit the scope of the invention as defined by the claims. Based on the above description a person skilled in the art will be able to modify the invention in many ways to provide immunochemical filter devices with a wide range of defined properties. It is obvious for a man skilled in the art that a filter device of the invention is possible to use together with or separately from the vessel described. The filter device could be used as a sieve above the analyzer device or it could be attached to or attachable to the analyzer device.

EXAMPLE 1

Respiratory Disorder

Example 1 relates to detection of *Streptococcus pyogenes* from a throat swab.

A solution of a labeled specific binding reagent is prepared by reacting a gold solution and *Streptococcus pyogenes* specific antibodies. Further a conjugate solution comprising gold labeled antibodies in 0.01-0.5 M glysine buffer pH 7.5 to 8.5 with BSA (0.1-1.0%), Tween 20 (0.01-0.05%) and trehalose (0.5-1.5%) is prepared and 20 µl of the conjugate solution is added to a POREX SQ-EASY™ filter tip comprising a high density polyethylene filter material with a particle retention of 15 µm. The solution is added to the filter material of the filter tip (the filter device of FIG. 1) using a pipette. The filter tip is then left to dry in a dry room, with a relative humidity less than 20%. The drying is continued in a dry room with a humidity of less than 8%.

The analyzer device of FIG. 3 is constructed by immobilizing a *Streptococcus pyogenes* specific antibody on the porous carrier to form a detection zone. A polyclonal antibody against the labeled specific binding reagent is immobilized on the carrier to form a control zone. The nitrocellulose is then blocked with a blocking solution comprising BSA (0.1-5.0%), TRITON-X-100, BRIJ and saccharose. The material is allowed to dry. The porous carrier is placed in a casing.

A buffer solution (extract) is prepared by adding 4 drops of extract solution A; 1-3 M NaNO3 and four drops of a extract solution B; 0.9% NaCl pH 1-3 to a tube just before the sample is taken. Then the sample is taken from the throat using a sterile swab and the swab is allowed to stand in the tube for two minutes after mixing. Then the swab is removed and the filter tin is attached to the tube.

Three drops (about 100-120 µl) of sample solution is pressed through the filter material and expressed therefrom into the sample well of the analyzer device. The complex formed of the sample and labeled specific binding reagent is allowed to migrate for 5 minutes after which the result is read in the test window. If red lines are visible both in the detection zone of the test window and in the control zone of the control window, it indicates the presence of *Streptococcus pyogenes* in the sample.

EXAMPLE 2

Multiple Channel Test for C-Reactive Protein

Example 2 describes use of the invention for C-reactive protein (CRP) and Myoglobin testing. The sample is tested for CRP and Myoglobin using a multiple channel analyzer device. The test for CRP is in one channel, the Myoglobin test in another and a control in a third channel.

A solution of labeled specific binding reagents is may be prepared by reacting latex particles which contain fluorchromogens inside the polystyrene particles with C-reactive protein (CRP) antibodies and with Myoglobin specific antibodies. A conjugate solution comprising gold labeled antibodies in 0.01-0.5 M glysine buffer pH 7.5 to 8.5 with BSA (0.1-1.0%), Tween 20 (0.01-0.05%) and trehalose (0.5-1.5%) is prepared and 40 µl is added to a high density polyethylene POREX SQ-EASY™ filter tip and the filter tip is then left to dry in a dry room, with a relative humidity less than 20%.

The analyzer device of with three separated channels is constructed by laser-etching the channels in a porous carrier of nitrocellulose and a mylar film. 0.2 µl of two different specific antibodies are immobilized on the porous carrier to form the detection zones in two channels of the analyzer device. An anti-mouse antibody for the labeled specific binding reagents is immobilized on the carrier in the third channel to form a control zone. The material is allowed to dry before the nitrocellulose is blocked with a blocking solution comprising BSA, HEXA and trehalose. The porous carrier is dried.

The amount of analyte to give a positive result is adjusted to 3 µl/ml for CRP and to 60 ng/ml for Myoglobin.

The test is performed by adding 500 ml of a modified PBS buffer, 1-5 mM EDTA and 10 ml of whole blood to a tube. The filter device is attached to the tube and three drops of the mixture of sample solution and conjugate solution is pressed trough the filter material of the filter tip and expressed therefrom to that place of the analyzer device were the sample should be placed. The sample and the labeled specific binding reagent are allowed to migrate for 5 minutes after which the result is read as visible dots in the control zone and in the detection zones, for samples where CRP and Myoglobin are present in amounts of 3 µl/ml and 60 ng/ml or more.

EXAMPLE 3

Multiple Channel Test for Virus Antigen Detection

Example 3 describes use of the present invention for detection of Virus antigens of Rotavirus and Adeno viruses.

A solution of two different labeled specific binding reagents were prepared by reacting a gold solution with specific antigens for Rotavirus and Adenovirus. 40 µl of a conjugate solution comprising the latex labeled antigens in 0.01-

0.5 M glysine buffer pH 7.5 to 8.5 with BSA (0.1-1.0%), Tween 20 (0.01-0.05%) and trehalose (0.5-1.5%) was prepared and added to a high density polyethylene POREX SQ-EASY™ filter tip. The filter tip was then left to dry in a dry room, with a relative humidity less than 20%. The drying is continued in a dry room with a humidity of less than 8%.

The analyzer device with three separated channels was constructed by forming the channels in a porous carrier of nitrocellulose and a mylar film 0.5 µl of two different antibodies were immobilized on the porous carrier to form the detection zones in two channels of the analyzer device. An anti-mouse antibody for the labeled specific binding reagents was immobilized on the carrier in the third channel to form a control zone. The reactive points of the channels were blocked and the analyzer device was dried.

100 mg of a faeces sample was added to a tube comprising 0.9 ml of a PBS pH 7.7 buffer solution. The sample and buffer solution was mixed and the filter tip was attached to the tube and the diluted sample and the conjugate solution of the filter device was pressed through the filter material and applied to the sample application spot of the analyzer device, from where the mixture diffused and migrated to the test zones, where a reaction took place if the sample contained the analyzable virus antigen and a visible dot or line could be seen.

EXAMPLE 4

Detection of *Escherichia coli* O157 and O111 in Food

Example 4 relates to a test for Enterohaemorrhagic *Escherichia coli* (EHEC).

The labeled specific binding reagent was prepared by reacting a gold solution and an *E. coli* O157 antibody. The conjugate solution and the filter tip were prepared according to example 1. An analyzer device comprising an *E. coli* O157 specific antibody in the detection zone was also prepared according to example 1. The filter tip and the analyzer device were hermetically dried and packed in a pouch together with a pipette.

25 mg of solid samples of meat and vegetables were homogenized in a Stomacher for 2 minutes in 225 ml of modified Trypticase-Soy Broth+Novobiocin and incubated on a rotary shaker (100 RPM) at 37° C. to 42° C. for 7 hours.

Pouches containing the devices were opened and 10 drops of the enriched samples were dispensed in tubes using a pipette. The filter tips were placed on the tubes. Three drops (approximately 110 ml) of sample solutions together with the conjugate of the filter devices were dispensed through the filter material into the sample window of the analyzer devices. The results were read 5 minutes after the application of the solution to the analyzer devices. Red lines were visible both in the detection zone of the test window and in the control zone of the control window, which indicated the presence of *E. coli* O157 in the sample.

Positive and negative control samples were used to check proper performance of the tests. 10 drops of a positive control solution were added to a filtering tube and the testing was performed as described above. After 5 minutes two visible lines were detected in the detection window and the control window.

10 drops of a negative control solution were added to a filtering tube and the testing was performed as described above. Only one visible line was detected in the control window.

EXAMPLE 5

Test for Celiac Disease

Example 5 relates to a test for celiac disease.

The labeled specific binding reagent was prepared by reacting a gold solution and a recombinant tissue transglutaminase. The conjugate solution and the filter tip were prepared according to Example 1. An analyzer device comprising an anti human IgA specific antibody in the detection zone was also prepared according to Example 1. The filter tip and the analyzer device were hermetically dried and packed in a pouch together with a tube containing 500 ml PBS buffer solution, a lancet, an alcohol pad and a plaster.

Positive and negative control samples were used. 1 drop (10 ml) of blood was added to a filtering tube containing 500 ml of buffer solution. The filter tip was attached to the tube and 3 drops of sample solution was transferred through the filter material to the analyzer device. After 5 minutes two visible lines were detected. One of the lines was in the detection window and the other was in the control window.

10 drops of a negative control solution were added to a filtering tube and the testing was performed as described above. Only one visible line was detected in the control window.

Performed at home the alcohol pad is used to wash a finger tip from which a blood sample is taken using the lancet. 1 drop of blood is transferred to the tube with the capillary. The test is performed as described above.

Based on the above description it is evident that use of filter devices of the present invention increases security of the test results due to the more controlled mobilization of the labeled specific binding reagent. Another advantage of the filter device is that tests can easily be performed for samples which need dilution and/or filtration. The samples may be added to a vessel already containing a buffer solution or an extraction buffer.

Further as the test system is easy to use it enables home use. Due to the fact that the analyzer device is not in direct contact with the liquid sample solution, overflow is avoided and an increased reliability of the test is obtained. Moreover the filter device and analyzer device of the invention are easy to store due to the fact that the devices are dried and that they are possible to store hermetically.

What is claimed is:

1. An immunochemical filter detection system comprising a test cassette, a cylindrical cap having a body, a closed end and an open end consisting of a filter material consisting essentially of a labeled binding reagent for analyte bound thereto in dry form, and a cylindrical sample collection vessel for receiving the filter material having an open end that is liquid tightly attachable to the open end of the cap and an opposing closed end, wherein the filter material protrudes outwardly from the open end of the cap and, is in a path for flow of sample thereinto when the cap is liquid tightly attached to the sample collection vessel, and has a particle retention of 10 to 20 micrometers, wherein the binding reagent is selected from the group consisting of an antibody, a recombinant antibody, an antigen, a lectin, a receptor, a ligand, fragments thereof and combinations thereof, and wherein further said labeled binding reagent and any analyte bound thereto are retained within said filter material until the cap is removed from the sample collection vessel, applied to an aperture in the test cassette and exposed to a binding reagent-free liquid analyte sample solution for migration through the filter material.

2. The immunochemical filter device according to claim 1 wherein said sample solution comprises a liquid sample mixed with a buffer solution.

3. The immunochemical filter device according to claim 1 wherein said filter material is selected from the group consisting of polyethylene, polyester, glass fiber and composites thereof.

4. The immunochemical filter device according to claim 1 wherein the label is selected from colored latex, gold, metal, dye, fluorogenic substances, superparamagnetic substances, chromogenic substances, fluorochromogens and enzymatic labels.

5. The immunochemical filter device according to claim 1 wherein said labeled binding reagent is included in a conjugate solution further comprising additives which act as stabilizers, release improvers and blocking agents.

* * * * *